United States Patent [19]

Krausz

[11] 4,051,127
[45] Sept. 27, 1977

[54] PREPARATION OF BENZODIAZEPINE DERIVATIVES

[75] Inventor: François Krausz, Montpellier, France

[73] Assignee: C M Industries, Paris, France

[21] Appl. No.: 646,515

[22] Filed: Jan. 5, 1976

[30] Foreign Application Priority Data

Jan. 6, 1975 United Kingdom .................. 485/75

[51] Int. Cl.² ........................................... C07D 291/08
[52] U.S. Cl. ..................... 260/239.3 D; 260/566 R; 560/35
[58] Field of Search .................... 260/239.3 D, 566 R, 260/471 A

[56] References Cited

U.S. PATENT DOCUMENTS

| | | | |
|---|---|---|---|
| 3,135,796 | 6/1964 | Layer et al. | 260/566 R |
| 3,441,607 | 4/1969 | Bell | 260/239.3 D |
| 3,751,412 | 8/1973 | Natsugari et al. | 260/566 R |
| 3,966,793 | 6/1976 | Schmitt | 260/239.3 D |

Primary Examiner—Henry R. Jiles
Assistant Examiner—Robert T. Bond
Attorney, Agent, or Firm—Stevens, Davis, Miller & Mosher

[57] ABSTRACT

A process for the manufacture of benzodiazepine derivatives which comprises reacting 2-amino-5-chloro-benzophenone with a primary amine $H_2N—R_1$ to give an imine which is reacted with an amino-ester

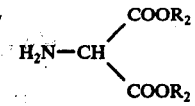

to give a ketimine said ketimine being then converted to a benzodiazepine derivative.

10 Claims, No Drawings

PREPARATION OF BENZODIAZEPINE DERIVATIVES

In its earlier patents (French Pat. No. 1,497,456 and Certificate of Addition No. 91,403; British Pat. Nos. 1,117,061, 1,117,062 and 1,117,063) in the name of Etablissements CLIN-BYLA, the applicant company had, inter alia, claimed a method for the preparation of benzodiazepine derivatives, starting from ortho-amino-benzonitriles.

The present invention relates to a new process for the manufacture of benzodiazepines which carry a carboxylic acid ester group in the 3-position, using, as the starting material, 2-amino-5-chloro-benzophenone, a commercially available and relatively cheap product.

This new method, which gives excellent yields, also possesses the advangate of involving a smaller number of steps which are represented in the equation below:

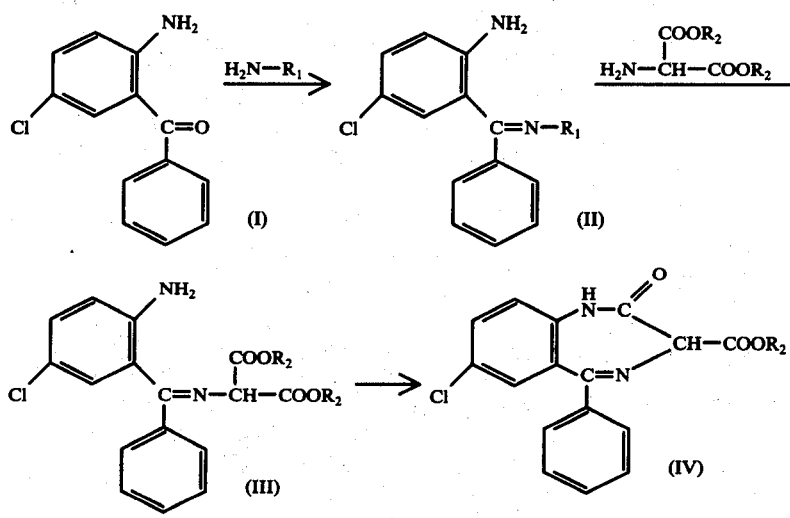

wherein $R_1$ represents an Alk—$NH_2$ group, an

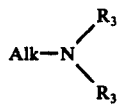

group or an Alk—$OR_4$ group in which Alk denotes a straight or branched alkylene group with 2 to 6 carbon atoms, $R_3$ and $R_4$ each represent a $C_1$-$C_4$ alkyl group, and $R_2$ represents a $C_1$-$C_4$ alkyl group.

The first step consists of condensing 2-amino-5-chlorobenzophenone with a highly basic primary amine $R_1$—$NH_2$ wherein $R_1$ has the meaning indicated above, so as to obtain the substituted imine (II). This reaction can be effected either by using an excess of amine as the solvent, or in an inert solvent such as toluene. The reaction temperature varies from 80° to 180°, the preferred temperature range being from 120° to 130°. Temperatures are expressed throughout in ° C. The amount of amine used can vary from 1 to 20 mols per mol of ketone depending on whether the reaction is carried out with or without a solvent. The amine can be used in the form of the free base or in the form of salts with acids such as the hydrochloride, the sulphate and the phosphate. This reaction is generally rather slow and can be very considerably accelerated by the addition of catalysts. The preferred catalysts include strong inorganic acids such as hydrogen chloride and concentrated sulphuric or phosphoric acid, and organic acids such as paratoluenesulphonic acid. Amine salts such as the hydrochloride, the sulphate or the phosphate either of the amine taking part in the reaction or of other amines such as triethylamine, pyridine or 2-methylimidazole can also be used as catalysts. Finally, it is also possible to use basic catalysts such as 2-amino-pyridine or 2-methyl-imidazole. The ketimine (II) is frequently obtained in the form of a mixture of the 2 syn- and anti-isomers. These isomers can be separated by conventional methods such as recrystallisation, distillation, chromatography and the like. However, this separation is not useful in practice and the subsequent reaction is carried out on the mixture of the 2 isomers.

The second step is a transamination reaction of the ketimine (II) by means of an aminoester

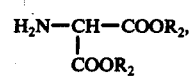

leading to the ketimines (III). The aminoester is used in the form of the base or, preferably, in the form of a salt such as the hydrochloride, the sulphate or the phosphate. The best results are obtained by using a slight excess of the aminoester salt. The reaction is carried out in a solvent such as benzene, toluene or dichloroethane, or in aliphatic alcohols, preferably methanol or ethanol, or in acetic acid. The reaction generally takes place at the boiling point of the solvent, except in the case of acetic acid when the reaction is carried out at a lower temperature, preferably around 60°. If the starting ketimine (II) was itself a mixture, the ketimine (III) is obtained in the form of a mixture of the syn- and anti-isomers. These isomers can be separated by known methods. This separation, however, serves no useful purpose in order to carry out the following step.

The latter consists of the cyclisation of the ketimines (III) to form benzodiazepines (IV) in accordance with the methods described in the earlier patents. These benzodiazepines, which carry a carboxylic acid ester group in the 3-position, possess valuable pharmacological properties which act on the central nervous system, and they are moreover used as starting materials for the preparation of other benzodiazepine derivatives as has been indicated in our previous patents.

The first two steps of the reaction sequence defined above are believed to be novel in themselves and are included within the scope of the invention as such.

The following examples illustrate the invention without limiting the scope thereof:

EXAMPLE 1

1-Phenyl-1-(2-amino-5-chloro-phenyl)-2,5-diazapent-1-ene a. Without a catalyst

5 g of 2-amino-5-chloro-benzophenone and 15 ml of ethylene-diamine are heated under reflux for 120 hours. The water produced in the course of the reaction is removed from the reaction medium as it is formed. To achieve this, the ethylene-diamine vapours which entrain the water pass, after condensation in a condenser, over a column of 4 A molecular sieve granules before returning to the reaction mixture.

When the reaction is complete, the product is evaporated to dryness and the residue is taken up in ether. The solution is washed with water, dried over sodium sulphate and evaporated to dryness.

5.9 g of imine are thus obtained and can be used directly or can be recrystallised from cyclohexane, yielding 5.1 g of crystalline imine.

Melting point $_k$ : 120°.

Nuclear magnetic resonance spectrum, in solution in deuterated chloroform, recorded at 60 M Hz (internal reference, tetramethylsilane). The chemical shifts δ are expressed in ppm relative to tetramethylsilane. The protons to which the signals are attributed are underlined.

10 H between 5.7 and 7.8 ppm (8 aromatic H and ArN$\underline{H}_2$)
2 H at 3.25 ppm (triplet C$\underline{H}_2$—N =)
2 H at 2.86 ppm (triplet C$\underline{H}_2$—NH$_2$)
2 H at 1.85 ppm (multiplet CH$_2$—N$\underline{H}_2$)

b. In the presence of hydrogen chloride

50 g of 2-amino-5-chloro-benzophenone are dissolved in 150 ml of ethylene-diamine and 11 g of dry hydrogen chloride are added by being bubbled in. The mixture is heated, with stirring, for 3 hours 30 minutes and is then evaporated to dryness, and the residue is taken up in 700 ml of ether. The solution is washed with 300 ml of water, then dried over sodium sulphate and evaporated to dryness. 59 g of imine, identical to that obtained in Example 1a, are obtained.

c. In the presence of triethylamine hydrochloride

A mixture of 5 g of 2-amino-5-chloro-benzophenone, 2.5 g of triethylamine hydrochloride and 15 ml of ethylenediamine is heated under reflux, with stirring, for 2 hours. The mixture is evaporated to dryness, and the residue is taken up in ether and washed with water. After drying over sodium sulphate and evaporating the solvent, 5.9 g of imine, identical to that of Example 1a, are obtained.

d. In the presence of 2-methyl-imidazole hydrochloride

A mixture of 5 g of 2-amino-5-chloro-benzophenone, 2.5 g of 2-methyl-imidazole hydrochloride and 13 ml of ethylene-diamine is heated under reflux for 2 hours. The water produced is removed as it is formed by passing over a molecular sieve as is indicated in Example 1a. The product is evaporated to dryness, the residue is taken up in 100 ml of water and extracted with ether. The ether solution is washed with water, dried over sodium sulphate and evaporated to dryness.

5.8 g of imine, identical to that of Example 1a, are obtained.

e. In the presence of para-toluenesulphonic acid

A mixture of 5 g of 2-amino-5-chloro-benzophenone, 4 g of ethylene-diamine and 0.2 g of para-toluenesulphonic acid in 100 ml of dry toluene is heated under reflux for 120 hours. The water formed in the course of the reaction is removed by azeotropic distillation. The product is evaporated to dryness and taken up in ether, and the paratoluenesulphonic acid is filtered off. After evaporation to dryness, 5.9 g of imine, identical to that of Example 1a, are obtained.

f. In the presence of 2-methyl-imidazole

20 g of 2-amino-5-chloro-benzophenone, 10 g of 2-methyl-imidazole and 50 ml of ethylene-diamine are heated under reflux for 24 hours, removing the water as it is formed by passing over a molecular sieve as indicated in Example 1a. The product is evaporated to dryness and the residue is taken up in ether. The solution is washed with water, dried over sodium sulphate and evaporated to dryness. 24.3 g of imine, identical to that of Example 1a, are obtained.

EXAMPLE 2

1-Phenyl-1-(2-amino-5-chloro-phenyl)-2,6-diazahex-1-ene

Following the methods described in Examples 1a to 1f, but replacing the ethylene-diamine by an equivalent amount of propylene-1,3-diamine, the desired imine is obtained in the form of a solid product consisting of a mixture of the syn- and anti-forms.

This product is characterised by its nuclear magnetic resonance spectrum, recorded under the conditions indicated in Example 1.

10 H between 6.60 and 7.5 ppm (8 aromatic H and ArN$\underline{H}_2$)
2 H at 3.30 ppm (triplet—C$\underline{H}_2$—N=)
2 H at 2.75 ppm (triplet—C$\underline{H}_2$—NH$_2$)
4 H at 1.75 ppm (multiplet—CH$_2$—C$\underline{H}_2$—CH$_2$—NH$_2$)

EXAMPLE 3

1-Phenyl-1-(2-amino-5-chloro-phenyl)-3-methyl-2,5-diaza-pent-1-ene and

1-Phenyl-1-(2-amino-5-chloro-phenyl)-4-methyl-2,5-diaza-pent-1-ene

The procedure of Example 2 is followed, replacing the propane-1,3-diamine by propane-1,2-diamine. A mixture of the 2 possible products is finally obtained and is characterised by its NMR spectrum.

10 H between 6.5 and 7.8 ppm (8 aromatic H and ArN$\underline{H}_2$)
3 H between 2.4 and 3.1 ppm

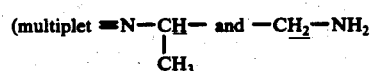

or

=N—C$\underline{H}_2$ and C$\underline{H}$—NH$_2$)
|
CH$_3$

2 H at 1.3 ppm (multiplet CH$_2$—N$\underline{H}_2$ and

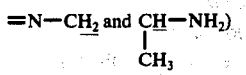

3 H at 1.05 ppm (doublet C$\underline{H}_3$)
No attempt was made to separate the constituents of the mixture since this separation is of no value on a practical basis, it being possible to use the mixture of the 2 imines directly for the subsequent reaction.

EXAMPLE 4

1-Phenyl-1-(2-amino-5-chloro-phenyl)-2,7-diazahept-1-ene

This product is prepared in accordance with the methods indicated in Example 1, using butane-1,4-diamine instead of ethylene-diamine.
Solid product, melting point: 143–8°
NMR spectrum:
10 H between 6.5 and 7.6 ppm (8 aromatic H and ArN$\underline{H}_2$)
2 H at 3.2 ppm (multiplet =N—C$\underline{H}_2$—)
2 H at 2.65 ppm (multiplet —C$\underline{H}_2$—NH$_2$)
6 H at 1.5 ppm (multiplet =N—CH$_2$—C$\underline{H}_2$—C$\underline{H}_2$—CH$_2$—N$\underline{H}_2$)

EXAMPLE 5

1-Phenyl-1-(2-amino-5-chloro-phenyl)-2,9-diazanon-1-ene

Product prepared according to the methods of Example 1, replacing the ethylene-diamine by hexane-1,6-diamine.
Gummy product.
NMR spectrum:
10 H between 6.55 and 7.80 ppm (8 aromatic H and ArN$\underline{H}_2$)
2 H at 3.25 ppm (triplet =N—C$\underline{H}_2$)
2 H at 2.65 ppm (triplet —C$\underline{H}_2$—NH$_2$)
10 H at 1.35 ppm (multiplet =N—CH$_2$—(C$\underline{H}_2$)$_4$—CH$_2$—N$\underline{H}_2$)

EXAMPLE 6

1-Phenyl-1-(2-amino-5-chloro-phenyl)-2-aza-5-oxa-hex-1-ene

The procedure of Example 1 is followed, replacing the ethylene-diamine by 2-methoxy-ethylamine.
It is possible to isolate the geometric isomers A and B easily from the crude product by recrystallisation from hexane and then from isopropyl ether.

Isomer A:
Melting point$_k$: 89°–90°, colourless crystals
U.V. spectrum (95° strength ethanol) λ$_{max}$: 247 nm ε: 24,000
NMR spectrum
8 H between 6.60 and 7.80 ppm (8 aromatic H)
6 H at 3.80 ppm (multiplet —C$\underline{H}_2$—C$\underline{H}_2$ and ArN$\underline{H}_2$)
3 H at 3.35 ppm (singlet —OC$\underline{H}_3$)
Isomer B:
Melting point$_k$: 98°–100°, colourless crystals
U.V. spectrum (95° strength ethanol) λ$_{max}$ 236 nm ε: 20,000 λ$_{max}$ 362 nm ε: 5,900
NMR spectrum
10 H between 6.5 and 7.5 ppm (8 aromatic H and ArN$\underline{H}_2$)
4 H at 3.5 ppm (multiplet C$\underline{H}_2$—C$\underline{H}_2$)
3 H at 3.3 ppm (singlet OC$\underline{H}_3$)

EXAMPLE 7

1-Phenyl-1-(2-amino-5-chloro-phenyl)-5-methyl-2,5-diaza-hex-1-ene

Following the methods of Example 1 and using 2-dimethylamino-ethylamine, the corresponding imine is obtained:
Yellow crystals, melting point$_k$: 89°–91°
NMR spectrum:
10 H between 6.5 and 7.6 ppm (8 aromatic H and ArN$\underline{H}_2$)
2 H at 3.40 ppm (triplet - C$\underline{H}_2$=N)
2 H at 2.60 ppm (triplet -

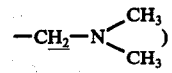

6 H at 2.2 ppm (singlet

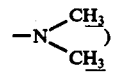

EXAMPLE 8

Diethyl [2-phenyl-2-(2-amino-5-chloro-phenyl)-1-aza-vinyl]-malonate a. In methanol and acetic acid
184 g of dry ethyl amino-malonate hydrochloride and 118 g of 1-phenyl-1-(2-amino-5-chloro-phenyl)-2,5-diazapent-1-ene are dissolved in 2,400 ml of methanol and 120 ml of acetic acid.
The mixture is heated under reflux for 2 hours and then the methanol is evaporated.
The acetic acid solution thus obtained can be used for the cyclisation reaction to form the benzodiazepine. If it is desired to isolate the intermediate imine, the acetic acid is evaporated in vacuo to leave a dry residue which is taken up in chloroform; the chloroform solution is washed with water, dried over sodium sulphate and evaporated to dryness.
The residue, which consists of a mixture of the syn- and anti-forms, possesses the following nuclear magnetic resonance spectrum:
10 H between 6.72 and 8.22 ppm (8 aromatic H and ArN$\underline{H}_2$)
1 H at 5.02 ppm (tertiary $\underline{H}$)
4 H at 4.52 ppm (2 quadruplets

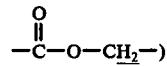

6 H at 1.57 ppm (2 triplets -

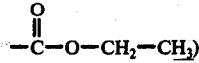

On recrystallisation from isopropyl ether, yellow crystals are obtained, melting point$_k$: 106°.

b. In dichloroethane 16 g of dry ethyl amino-malonate hydrochloride are suspended in 200 ml of dichloroethane, then a solution of 10 g of 1-phenyl-1-(2-amino-5-chloro-phenyl)-2,5-diazapent-1-ene in 100 ml of dichloroethane is added and the whole is heated at 80° for 3 hours 30 minutes. The red colour at the start changes to yellow at the end of the reaction.

It is not necessary to isolate the product in the solid state, it being possible to use the solution directly for the cyclisation reaction.

However, in the same manner as above, it is possible to isolate a product which is identical both with regard to its NMR spectrum and with regard to its melting point after recrystallisation from isopropyl ether.

EXAMPLE 9

7-Chloro-3-ethoxycarbonyl-5-phenyl-2-oxo-2,3-dihydro-1H-benzo-1,4-diazepine (4279 CB)

a. The crude product originating from Example 8a is dissolved in 2,200 ml of acetic acid and the solution is heated at 80°, with stirring, for 2 hours.

The solution is evaporated to dryness in vacuo and the residue is taken up in 1 liter of dichloromethane. The solution is washed twice with 2 liters of water, then dried over sodium sulphate and evaporated to dryness.

The residue is taken up in 200 ml of ether and, after stirring for 15 minutes, the crystals of 4279 CB (98 g) are filtered off. Melting point$_k$: 244°.

The overall yield, calculated from the starting 2-amino-5-chloro-benzophenone without purification of the intermediate products, is 66.5%.

b. The solution is dichloroethane obtained in Example 8b is concentrated by distilling 50 ml of solvent.

After cooling to 15°, 9 g of dry hydrogen chloride are dissolved in the solution, by being bubbled in. The mixture is left at ambient temperature for 15 minutes and is then heated at 80° for 3 hours, and the hydrogen chloride is removed by bubbling in nitrogen. The solution is cooled to 5° and neutralised to pH 8–9 by means of dry ammonia. After removing the excess ammonia in the form of a gas, 50 ml of dichloromethane are added and the organic phase is washed with 50 ml of water. The solution is dried over sodium sulphate and evaporated to dryness. The residue is taken up in 50 ml of ether and 9.5 g of crystals of 4279 CB are filtered off, melting point$_k$: 244°.

Overall yield, calculated from 2-amino-5-chlorobenzophenone: 79%.

c. The crude 1-phenyl-1-(2-amino-5-chloro-phenyl)-2,5-diaza-pent-1-ene obtained from 50 g of 2-amino-5-chlorobenzophenone according to Example 1b, is taken up in 300 ml of acetic acid.

92 g of dry ethyl amino-malonate hydrochloride are added and the mixture is heated at 60°, with stirring, for 2 hours 45 minutes and then at 80° for 1 hour. The acetic acid is evaporated in vacuo and the residue is taken up in 500 ml of methylene chloride. The solution is washed with 300 ml of water, dried over sodium sulphate and evaporated to dryness in vacuo. The residue is taken up in 200 ml of ether and the mixture is stirred for 15 minutes. The crystals (48.5 g) are filtered off, melting point$_k$: 244°. Overall yield relative to 2-amino-5-chloro-benzophenone: 65.5%.

What is claimed is:

1. A process for the manufacture of benzodiazepines of formula (IV)

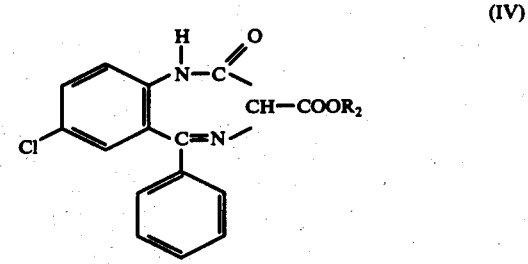

(IV)

which process comprises:

i. condensing 2-amino-5-chloro-benzophenone (I) with a

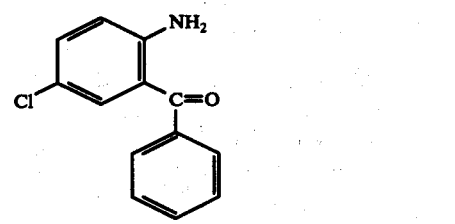

(I)

primary amine R$_1$—NH$_2$ to give an imine (II)

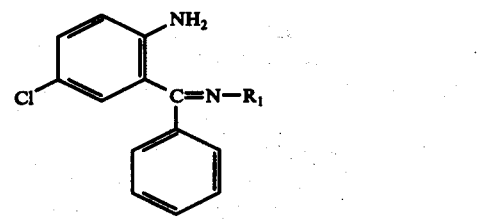

(II)

ii. reacting the imine (II) with an amino ester

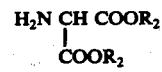

H$_2$N CH COOR$_2$
   |
   COOR$_2$ to give a ketimine (III),

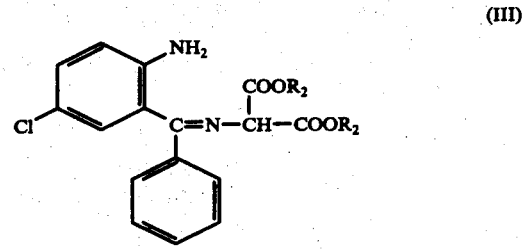

(III)

and iii. converting the ketimine (III) to the benzodiazepine (IV) by cyclization, and in which R$_1$ represents an Alk—NH$_2$ group, an

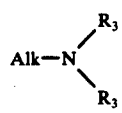

group or an Alk—OR₄ group in which Alk denotes a straight or branched alkylene group with 2 to 6 carbon atoms and R₃ and R₄ each represent a C₁-C₄ alkyl group and R₂ represents a C₁-C₄ alkyl group.

2. A process as claimed in claim 1, wherein step (i) is performed by admixing one molar part of the 2-amino-5-chlorobenzophenone with from 1 to 20 molar parts of the primary amine R₁NH₂, either as the free base or as an acid addition salt, and maintaining the mixture at a temperature of from 80° to 180° C.

3. A process as claimed in claim 1 in which a catalyst selected from the group consisting of a strong inorganic acid, an organic acid, an amine salt or an organic base is used in step (i).

4. A process as claimed in claim 2 in which step (i) is carried out at a temperature in the range of 120° to 130° C.

5. A process as claimed in claim 1 wherein step (ii) is performed by admixing the imine (II) with the amino-ester H₂N CH(COOR₂)₂ in a solvent for the reactants and heating the mixture at a temperature up to its reflux temperature.

6. A process as claimed in claim 1 in which the amino-ester in step (ii) is present as an acid addition salt and in slight excess.

7. A process as claimed in claim 5 in which when acetic acid is used as the solvent in step (ii) the reaction temperature is in the order of 60° C.

8. A process for the manufacture of benzodiazepines of formula (IV) which process comprises:
  i. admixing one molar part of 2-amino-5-chloro-benzophenone (I) with from 1 to 20 molar parts of a primary amine R₁—NH₂, either as the free base or as an acid addition salt and a catalyst selected from the group consisting of a strong inorganic acid, an organic acid, an amine salt or an organic base in a solvent for the reactants, maintaining the mixture at a temperature of from 80° to 180° C and removing water from the reaction mixture as it is formed to give an imine (II),
  ii. admixing the imine (II) with an amino-ester

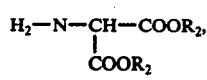

either as the free base or as an acid addition salt, in solvent for the reactants and heating the mixture at a temperature up to its reflux temperature to give a ketimine (III),
  iii. heating the ketimine (III) to give a benzodiazepine (IV), and and in which R₁ and R₂ and (I), (II), (III) and (IV) are as defined in claim 1.

9. In a process for the manufacture of benzodiazepines which comprises condensing 2-amino-5-chloro-benzophenone with an amine to produce an imine, reacting the imine with an amino ester to produce a ketamine and converting the ketamine to said benzodiazepine by cyclization, the improvement wherein the 2-amino-5-chloro-benzophenone is reacted with an amine having the formula R₁—NH₂ wherein R₁ is Alk—NH₂,

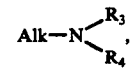

or Alk—OR₄ and Alk is a straight or branched alkylene group having 2 to 6 carbon atoms and R₃ and R₄ are alkyl groups having 1 to 4 carbon atoms.

10. A process for making a ketimine of the formula

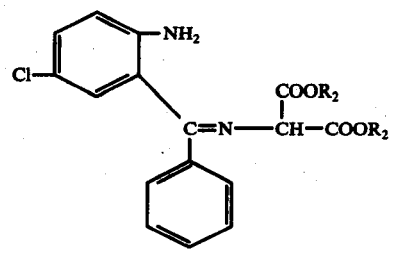

which comprises reacting an imine of the formula

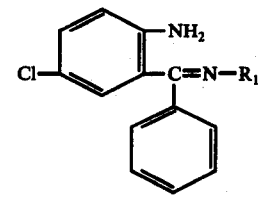

wherein R₁ is Alk—NH₂,

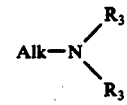

or Alk—OR₄ and Alk is a straight or branched alkylene group with 2 to 6 carbon atoms and R₃ and R₄ are alkyl groups of 1 to 4 carbon atoms with an amino ester having the formula

wherein R₂ is an alkyl group having 1 to 4 carbon atoms.